United States Patent [19]

Alam et al.

[11] Patent Number: 4,915,956

[45] Date of Patent: Apr. 10, 1990

[54] LIQUID CISPLATIN FORMULATIONS

[75] Inventors: Abu S. Alam, Libertyville; Shaila Battu, Villa Park; Jairaj U. Mehta, Forest Park; Fakrul A. A. Sayeed, Mundelein; John N. Kapoor, Lake Forest, all of Ill.

[73] Assignee: Lyphomed, Inc., Rosemont, Ill.

[21] Appl. No.: 133,516

[22] Filed: Dec. 16, 1987

[51] Int. Cl.⁴ .................................. A61K 33/24
[52] U.S. Cl. .................................. 424/649
[58] Field of Search ..................... 424/131, 649

[56] References Cited

U.S. PATENT DOCUMENTS 4,310,515  1/1982  Granatek et al. ............... 424/131
4,451,447  5/1984  Kaplan et al. .................. 424/131

*Primary Examiner*—Jerome D. Goldberg
*Attorney, Agent, or Firm*—Leydig, Voit & Mayer

[57] ABSTRACT

This invention relates to an injectable, stable, sterile aqueous solution of cisplatin in a unit dosage form in a sealed container, the solution being suitable for administration by the injection thereof into man upon the removal thereof from the container, the solution consisting of water and cisplatin, said solution having a concentration of cisplatin between about 0.1 and about 1.3 mg/mL, and a pH in the range of about 3.5 to about 5.0, the solution being substantially free of dissolved oxygen.

10 Claims, No Drawings

LIQUID CISPLATIN FORMULATIONS

BACKGROUND OF THE INVENTION

The present invention relates to cisplatin, in general, and in particular to injectable formulations of cisplatin in a unit dosage form.

Cisplatin was first synthesized in 1845 and its cytotoxic properties were reported in 1967 when it was first discovered that cisplatin inhibited cell division. Subsequent animal studies revealed that cisplatin had anti-neoplastic activity. Since cisplatin's introduction into initial clinical trials in the 1970's, it has now grown into one of the most widely used chemotherapy agents for the treatment of various solid tumors. The use of cisplatin for the treatment of tumors is the subject of U.S. Pat. No. 4,177,263.

Cisplatin, since its commercial introduction, has been available only as a lyophilized powder which must be reconstituted with an aqueous solution, such as saline or dextrose, prior to use. However, the aqueous solution necessitates prompt administration in that the shelf life is limited to several hours after preparation. Although the lyophilized product has several advantages, it also suffers from several disadvantages, as well.

The lyophilized product must be reconstituted which by necessity requires some degree of personnel exposure. This is particularly undesirable when the drug is a strong cytotoxic anti-neoplastic agent. This hazardous personnel exposure is aggravated by aerosilization of the potent cytotoxic agent. The dissolution of the lyophilizate necessitates additional entry into the vial with a syringe to add solubilizing agent and with each accession of the vial small quantities become airborne, the result being known as aerosolization. The added exposure requires particular precautions, such as the use of rubber gloves and masks. Furthermore, reconstitution introduces the potential for dilution errors. Because of the foregoing reasons, producers and consumers alike prefer readily injectable liquid formulations of parenterally administered drugs.

Because of the desirability of a liquid formulation of cisplatin, efforts have been made to develop such formulations. In this respect, reference is made to U.S. Pat. Nos. 4,310,515 and 4,451,447. The '515 patent is concerned with certain aqueous solutions of cisplatin, whereas the '447 patent concerns liquid cisplatin formulations in which the solvent comprises polyethylene glycol or methoxypolyethylene glycol, or mixtures thereof, in combination with water. The latter compounds suffer from the disadvantage that they themselves introduce undesirable organic products as part of the administration of the active agent. On the other hand, while the compositions of the '515 patent do not introduce an organic material, upon injection, they do suffer from the disadvantage that they are extremely acidic in nature, with the pH being in the range of 2.0 to 3.0, a pH of 2.5 being preferred.

Of course, for solutions for injection, one consideration is the patient comfort, upon infusion of the product. One of the factors which impacts patient comfort is the pH of the infused solution. Therefore, it is generally recognized that the closer the pH is to that of blood (7.4), the less likelihood of patient discomfort upon infusion. A disadvantage of the compositions of the '515 patent then is that the pH of the formulations is highly acidic, the pH being substantially lower than that of blood. Besides general patient discomfort, such a low pH can cause localized phlebitis at and around the site of injection.

A need has therefore existed for a liquid cisplatin formulation which causes less patient discomfort, upon infusion, and which possesses sufficient stability such that it can be manufactured, stored, and used, without substantial degradation.

SUMMARY OF THE INVENTION

It now has been surprisingly found that cisplatin formulations comprised of from about 0.1 to about 1.3 mg/mL of cisplatin, per mL of solution when adjusted to a pH of about 3.5 to about 5.0 are sufficiently stable, in the substantial absence of dissolved oxygen, to be capable of being formulated into unit dosage forms which can be manufactured, stored, and used, without substantial degradation of the cisplatin.

In accordance with the present invention there is provided an injectable, stable, sterile aqueous solution of cisplatin in a unit dosage form in a sealed container, the solution being suitable for administration by the injection thereof into man upon the removal thereof from the container; the solution having a concentration of cisplatin between about 0.1 and about 1.3 mg/mL, a pH in the range of about 3.5 to about 5.0 and containing from about 4.5 to about 9 mg/mL of sodium chloride; the solution being substantially free of dissolved oxygen; and the sealed container being characterized in that it does not function as a metal ion source during the course of storage of the solution.

DETAILED DESCRIPTION OF A PREFERRED EMBODIMENT

As indicated, the present invention provides an aqueous solution of cisplatin. The cisplatin which is used in accordance with the present invention may be obtained from any commercial source or may be synthesized in a manner known in the art. The cisplatin composition should be substantially pure and free of heavy metals.

Further, the formulations should be substantially free of dissolved oxygen. As used in the present application, the phrase "substantially free of dissolved oxygen" means having less than about 10 ppm of dissolved oxygen present. Preferably, the amount of dissolved oxygen will be less than about 2 ppm. The reason why the dissolved oxygen has an adverse effect upon the stability of formulations containing cisplatin is not understood. It is assumed that the dissolved oxygen somehow interacts with the cisplatin molecule in some fashion, causing degradation thereof.

The amount of cisplatin used in the formulations in accordance with the present invention vary from about 0.1 to about 1.3 mg/mL. The amount which is present is not critical and may be adjusted in accordance with the individual needs and preferences. Typically, the concentration of the cisplatin will be about 1.0 mg/mL.

The composition of the present invention also comprises sodium chloride. The sodium chloride functions as an isotonic agent to render the final products compatible with blood and body tissue. In this respect, the amount of sodium chloride should preferably be sufficient to render the final product substantially isotonic, in order to achieve maximum patient comfort. It is also believed that the chloride has a stabilizing effect upon the cisplatin. Amounts of sodium chloride of about 9 mg/mL, however, are sufficient to render the necessary stabilizing effect afforded by the chloride ions. As such a level renders the solutions isotonic, no need is seen to use lesser amounts of sodium chloride, which might result in a less stable product. Thus, although sufficiently stable formulations could result from the use of sodium chloride in amounts somewhat less than 9 mg/mL, no advantage would result and the product would not be isotonic.

The solutions of the present invention in order to achieve the desired stability, while providing a composition which is approaching the pH of human blood, will have a pH from about 3.5 to about 5.0. Preferably, the pH will be about 4.0. The pH of the formulations of the present invention is typically achieved through adjustment with a suitable acid. Preferably, the acid employed will be hydrochloric acid although other acids may be employed.

It is required to remove oxygen from the environment to maximize the stability of the resultant formulation. Thus, in a typical process for manufacturing the formulations used in the present invention, a desired amount of water will be placed into a sparging system, through which nitrogen can be bubbled. The nitrogen sparging will continue until the oxygen content is below about 10 ppm, preferably below about 2 ppm. After the water has been suitably sparged, the desired amount of sodium chloride will be added thereto and mixed until it is dissolved. After the sodium chloride has been dissolved, the desired amount of cisplatin will be added to the aqueous sodium chloride solution and mixed until completely dissolved. At that time the pH of the formulation may be analyzed, the volume increased to that ultimately desired and the pH adjusted to a final level, usually from about 3.5 to about 5.0, preferably about 4.0, typically employing hydrochloric acid at a concentration of about 10 percent (v/v), for purposes of making the pH adjustment.

After formulation, the solution is transferred into individual unit vials, typically having a vial size from about 10 mL to about 200 mL. The entire process of making the formulations used in the present invention as well as filling them into vials should be done in equipment which is substantially free of metals or metal ions. Thus, glass mixing vessels and stirrers and glass or plastic filling equipment are preferred.

The cisplatin formulations, after filling, should be sealed. Typically, the vials will be sealed with stoppers which do not themselves act as a source of metal ion contamination. One manner of obtaining stoppers which do not act as a source of metal contamination is to place the stoppers into a suitable container and to treat them with a solution of ethylenediamine tetraacetic acid (EDTA). Subsequently, the stoppers may be autoclaved at an elevated temperature, such as 121° C., for a substantial length of time, such as 15 minutes. The stoppers should then be rinsed with water, at least three times. By treating the stopper with the EDTA, the metal ions from the stopper surface are complexed into soluble salts and removed by the washing process. Thus, metal ions are unavailable for leaching into the liquid formulation, causing contamination of the cisplatin solution. Also during the processing of the formulations of the present invention it is desired to sterilize the same. This most typically may be achieved by passing the cisplatin solution through an appropriate sterilization filter, such as a 0.22 micron filter.

The formulations of the present invention provide a number of important advantages. The liquid formulations provide a simple method of dosing, as compared to the only presently commercially available product, a lyophilized form of cisplatin. Further, when compared to the formulations of U.S. Pat. No. 4,310,515, the pH of the formulation of the present invention is closer to that of blood, resulting in less patient discomfort, upon infusion, than the formulations of U.S. Pat. No. 4,310,515 which have an extremely acidic pH of 2.0 to 3.0. Such a low pH can cause localized phlebitis at and around the site of injection.

In addition to the ingredients specified as being present in the formulations of the present invention, other harmless, physiologically acceptable excipients may be present.

The liquid cisplatin formulations of the present invention, which are provided in unit dosage forms are characterized in that upon storage at room temperature, for period of at least 2 years, they will lose less than 10 percent of their initial cisplatin potency, preferably less than about 5 percent, as determined by high performance liquid chromatagraphy (HPLC). The analytical procedure for determining cisplatin potency is as follows:

PROCEDURE: Sodium Chloride Diluent—Dissolve 9.0 g of reagent grade Sodium Chloride in 1 L of water and mix thoroughly.

Standard Preparation—Weigh accurately about 50 mg, on the anhydrous basis, of Cisplatin Reference Standard into a 100 mL volumetric flask and dilute with about 95 mL sodium chloride diluent. Shake until completely dissolved, then q.s. to volume with sodium chloride diluent. Store in an amber bottle at 4° C., discard after one week.

ASSAY PREPARATION: I. Cisplatin for Injection:

Reconstitute the lyophilized finished product with sodium chloride diluent and quantitatively transfer to a volumetric flask to obtain a final concentration of about 0.5 mg/mL cisplatin. Shake until completely dissolved.

II. Cisplatin Injection:

The concentration of cisplatin in Cisplatin Injection is such that no dilution is required.

System Suitability Preparation—Prepare an 0.5 mg/mL solution of Cisplatin in water 24 to 48 hours before analysis.

Mobile Phase—Prepare a suitable, filtered degassed mixture of methanol and buffer (88:12). The buffer portion is 1.0% sodium acetate adjusted to pH of 5.60 with acetic acid. The strength of buffer can be decreased to meet system suitability requirements (see System Suitability).

Chromatographic System—Typically a high pressure liquid chromatograph, operated at room temperature, is fitted with two stainless steel columns. The first column contains packing L9 and the second L14. The mobile phase is maintained at a flow rate of 2.0–3.0 mL/min. An ultraviolet detector that monitors absorption at 301 nm is used.

System Suitability Test—Chromatograph 5 replicate injections of standard preparation and record the peak responses of cisplatin. The relative standard deviation is not more than 1.5%.

Inject 100 mcL of the system suitability preparation and calculate the resolution factor between the cisplatin peak and its aquation products peak. The resolution factor is calculated as follows:

$$R = \frac{2(t_2 - t_1)}{W_1 + W_2}$$

where $t_1$ and $t_2$ are the retention times measured from the time of injection to the time of elution of the peaks and $W_1$ and $W_2$ are the widths of the peaks measured by extrapolating the relatively straight sides to the baseline. The resolution factor must be greater than 2.0.

If the resolution is under 2.0, then the mobile phase buffer concentration can be lowered as low as 0.5% to achieve an adequate resolution factor.

Procedure—Separately inject 50 mcL of the standard preparation and the assay preparation into the chromatograph, record the chromatograms and measure the peak response for cisplatin.

CALCULATIONS: Calculations the concentration in mg/mL, of $Cl_2H_6N_6Pt$ in the sample of Cisplatin for Injection or Cisplatin Injection taken the formula:

$$A = C (R_u/R_s) D.F.$$

where:
 C=Concentration of the cisplatin in the Standard Preparation in m9/mL.
 $R_u$=Peak response of the Assay Preparation.
 $R_s$=Peak response of the Standard Preparation.
 D.F.=The dilution factor for the sample.
Then calculate the percent claim:

$$\% \text{ Claim} = A \times \frac{100\% \text{ Claim}}{B}$$

where B is the claim of Cisplatin for Injection in mg/vial or the claim of Cisplatin Injection in mg/mL.

The present invention will be further described by way of the following non-limiting examples.

EXAMPLE 1

This example demonstrates a commercial process for the manufacture of cisplatin formulations in accordance with the present invention, the formulations having a cisplatin concentration of 0.5 mg/mL, in a unit dosage form, 20 mL sealed vials.

Eight liters of water for injection, USP were transferred through a nitrogen sparaging system into a glass-lined tank. 90 grams of sodium chloride was added thereto, with mixing, until the sodium chloride was dissolved. Thereafter, 5.04 grams of cisplatin (potency 99.2 percent) was added to the sodium chloride solution and mixed until dissolved. The pH was checked and found to be 6.3. The volume in the vessel was then increased to 9.5 liters, with water for injection, USP, having an oxygen content below ppm. The pH of the solution was then adjusted to 3.8 plus or minus 0.1 percent with 10 percent (v/v) hydrochloric acid, amounting to 3 milliliters of the 10 percent hydrochloric acid. The final volume was increased to 10 liters, again with water for injection, USP, having oxygen content less then 2 ppm. The resultant formulation was then passed through a sterile 0.22 micron filter and filled into 20 mL vials. The vials were stoppered and subjected to storage at both room temperature and 40° C. The stoppers which were employed were supplied by the West Company. The stoppers had previously been rinsed with water for injection, USP, placed into a container and covered with a solution of 25 mg of disodium EDTA. After being covered with the EDTA solution, the stoppers were autoclaved at 121° C. for 15 minutes and subsequently washed approximately three times with water for injection, USP. By treating the stoppers with the EDTA formulation, the metal components within the stopper were complexed by the EDTA and were removed by the washing step. Thus, the metal ions were unavailable for migration into the cisplatin solution. The storage results of this formulation are shown in Table I.

EXAMPLE 2

In a manner similar to that set forth in Example 1, a 0.5 mg/mL solution of cisplatin containing 9 mg/mL of sodium chloride was made, having a pH of 3.8. The formulation was filled into 20 mL vials and stoppered with a stopper treated with EDTA in the same manner as the stopper in example 1. The vials of this example were subjected to storage at room temperature and 40° C. and the storage results are set forth in Table I.

EXAMPLE 3

In a manner similar to that of Example 1, a formulation containing 0.5 mg/mL of cisplatin was prepared, containing 9 mg/mL of sodium chloride. The solution had a pH of 3.8 and the solution was filled to a level of 40 mL and 50 mL vials and stoppered in the same manner as in example 1. The vials of this example were subjected to storage at room temperature and 40° C. and the results of the storage study are set forth in Table I.

EXAMPLE 4

In a manner similar to that of Example 1, a formulation containing 0.5 mg/mL of cisplatin and 9 mg/mL of sodium chloride, having a pH of 3.8 was prepared. The formulation of this example was used to fill 100 mL vials and were stoppered in the same manner as Example 1. The vials of this example were subjected to storage at room temperature and 40° C. and the results of the storage study are set forth in Table II.

. EXAMPLE 5

In a manner similar to that of Example 1, a formulation containing 1.0 mg/mL cisplatin and 9 mg/mL sodium chloride, having a pH of 4.0 was prepared. The formulation of this example was used to fill 20 mL vials to a level of 10 mL which were stoppered in the same manner as in Example 1. The vials of this example were subjected to storage at room temperature and 40° C. and the results of the storage study are set forth in Table II.

EXAMPLE 6

In a manner similar to that of Example 1, a formulation containing 1.0 mg/mL of cisplatin was prepared, containing 9mg/mL of sodium chloride. The solution had a pH of 3.9 and was filled to a level of 20 mL in 50 mL vials and stoppered in the same manner as in Example 1. The vials of this example were subjected to storage at room temperature and 40° C. and the results of the storage study are set forth Table II.

EXAMPLE 7

In a manner similar to that of Example 1, a formulation containing 1.0 mg./mL of cisplatin was prepared, containing 9 mg/mL sodium chloride. The solution had a pH of 3.9 and was filled to a level of 50 mL in 100 mL vials and stoppered in the same manner as in Example 1. The vials of this example were subjected to storage at room temperature and 40° C. and the results of the storage study are set forth in Table II.

EXAMPLE 8

In a manner similar to that set forth in Example 1, a 1.0 mg/mL solution of cisplatin containing 9 mg/mL of sodium chloride was prepared, having a pH of 3.9. The formulation was filled into 200 mL vials, to a level of 100 mL, and stoppered in the same manner as in Example 1. The vials of this example were subjected to storage at room temperature and 40° C. and the results of the storage study are set forth in Table II.

COMPARATIVE EXAMPLE 9

In a manner similar to that of Example 1, a formulation containing 1.0 mg/mL of cisplatin was prepared, containing 9 mg/mL of sodium chloride. The solution has a pH of 2.5 and was filled to a level of 10 mL in 20 mL vials and stoppered in the same manner as in Example 1. The vials of this example were subjected to storage at room temperature and 40° C. and the results of the storage are set forth in Table III.

From the foregoing examples, it is quite apparent that the formulations of the present invention upon storage at room temperature for periods of three months, or more, have maintained substantially all of their original potency. Further, the solutions have maintained their original clarity and therefore after such period of storage remain suitable for injection. Such stability of the formulations of the present invention can be compared to that of the formulation of Comparative Example 9 in which the initial pH was 2.5, the preferred pH described in U.S. Pat. No. 4,310,515. Contrary to the teachings of that patent, the compositions of the present invention, having a less acidic pH, and therefore being more pharmaceutically acceptable, have been shown to be at least as stable. This discovery is purely surprising in view of the explicit teachings of the '515 patent which indicate that formulations with a pH above 3.0 would be unstable, from the standpoint of maintaining cisplatin potency.

TABLE I

| | | | \multicolumn{5}{c}{CISPLATIN INJECTION STABILITY 0.5 mg/ml} |
|---|---|---|---|---|---|---|---|
| | | | Zero Time | One Month | Two Month | Three Month | Four Month |
| Example 1 | Room Temp. | Assay | 107.3 | — | — | — | 103.0 |
| | | pH | 3.9 | — | — | — | 4.4 |
| | | Clarity | Clear | — | — | — | Clear |
| | 40° C. | Assay | 107.3 | — | — | — | 98.1 |
| | | pH | 3.9 | — | — | — | 4.9 |
| | | Clarity | Clear | — | — | — | Clear |
| Example 2 | Room Temp. | Assay | 104.0 | 102.8 | 103.0 | 102.2 | — |
| | | pH | 3.7 | 3.8 | 4.0 | 4.1 | — |
| | | Clarity | Clear | Clear | Clear | Clear | — |
| | 40° C. | Assay | 104.0 | 102.9 | 102.2 | 101.0 | — |
| | | pH | 3.7 | 4.1 | 4.2 | 4.5 | — |
| | | Clarity | Clear | Clear | Clear | Clear | — |
| Example 3 | Room Temp. | Assay | 104.3 | 104.2 | 103.9 | 103.3 | — |
| | | pH | 3.7 | 3.8 | 3.7 | 3.9 | — |
| | | Clarity | Clear | Clear | Clear | Clear | — |
| | 40° C. | Assay | 104.3 | 102.4 | 102.4 | 101.6 | — |
| | | pH | 3.7 | 4.2 | 4.4 | 4.5 | — |
| | | Clarity | Clear | Clear | Clear | Clear | — |
| Example 4 | Room Temp. | Assay | 100.9 | 101.7 | 101.2 | 100.7 | — |
| | | pH | 3.7 | 3.7 | 3.6 | 3.6 | — |
| | | Clarity | Clear | Clear | Clear | Clear | — |
| | 40° C. | Assay | 100.9 | 100.9 | 100.1 | 101.4 | — |
| | | pH | 3.7 | 4.1 | 4.1 | 4.4 | — |
| | | Clarity | Clear | Clear | Clear | Clear | — |

TABLE II

| | | | \multicolumn{4}{c}{CISPLATIN INJECTION STABILITY 1.0 mg/mL} |
|---|---|---|---|---|---|---|
| | | | Zero Time | One Month | Two Month | Three Month |
| Example 5 | Room Temp. | Assay | 98.5 | 97.3 | 99.1 | 98.4 |
| | | pH | 4.0 | — | — | 4.0 |
| | | Clarity | Clear | Clear | Clear | Clear |
| | 40° C. | Assay | 98.5 | 46.6 | 96.6 | 99.3 |
| | | pH | 4.0 | — | — | 4.0 |
| | | Clarity | Clear | Clear | Clear | Clear |
| Example 6 | Room Temp. | Assay | 98.3 | 96.6 | 100.6 | 99.6 |
| | | pH | 3.9 | — | — | 4.0 |
| | | Clarity | Clear | Clear | Clear | Clear |
| | 40° C. | Assay | 98.3 | 96.5 | 98.2 | 98.6 |
| | | pH | 3.9 | — | — | 4.2 |
| | | Clarity | Clear | Clear | Clear | Clear |
| Example 7 | Room Temp. | Assay | 100.7 | 98.9 | 101.2 | 101.0 |
| | | pH | 3.9 | 3.9 | 4.0 | 4.0 |
| | | Clarity | Clear | Clear | Clear | Clear |
| | 40° C. | Assay | 100.7 | 98.9 | 101.1 | 100.5 |
| | | pH | 3.9 | 4.0 | 4.0 | 4.1 |
| | | Clarity | Clear | Clear | Clear | Clear |
| Example 8 | Room Temp. | Assay | 100.2 | 99.3 | 101.6 | 100.4 |
| | | pH | 3.9 | 3.8 | 4.0 | 3.9 |
| | | Clarity | Clear | Clear | Clear | Clear |
| | 40° C. | Assay | 100.2 | 99.8 | 100.9 | 100.4 |
| | | pH | 3.9 | 3.9 | 4.1 | 4.0 |

TABLE II-continued

CISPLATIN INJECTION STABILITY 1.0 mg/mL

| | Zero Time | One Month | Two Month | Three Month |
|---|---|---|---|---|
| Clarity | Clear | Clear | Clear | Clear |

TABLE III

CISPLATIN INJECTION STABILITY 10 mg/mL pH - 2.5

| | | | Zero Time | One Month |
|---|---|---|---|---|
| Comparative Example 9 | Room Temp. | Assay | 99.3 | 98.2 |
| | | pH | 2.5 | 2.3 |
| | | Clarity | Clear | Clear |
| | 40° C. | Assay | 99.3 | 97.1 |
| | | pH | 2.5 | 2.3 |
| | | Clarity | Clear | Clear |

What is claimed is:

1. An injectable, stable, sterile aqueous solution of cisplatin in a unit dosage form in a sealed container, the solution being suitable for administration by the injection thereof into man upon the removal thereof from the container, the solution consisting of water and cisplatin, said solution having a concentration of cisplatin between about 0.1 and about 1.3 mg/mL, and a pH in the range of about 3.5 to about 5.0, the solution being substantially free of dissolved oxygen.

2. The composition of claim 1 wherein the amount of dissolved oxygen which is present is below about 2 ppm.

3. The composition of claim 1 wherein the vials are sealed with a stopper which has been treated with ethylenediamine tetraacetic acid to complex any heavy metals contained therein.

4. An injectable, stable, sterile aqueous solution of cisplatin in a unit dosage form in a sealed container, the solution being suitable for administration by the injection thereof into man upon the removal thereof from the container, the solution consisting of water, cisplatin, and sodium chloride, said solution having a concentration of cisplatin between about 1 and about 1.3 mg./mL, and a pH in the range of about 3.5 to about 5.0, the solution being substantially free of dissolved oxygen.

5. The solution of claim 4 further comprising from about 4.5 mg to about 9 mg/mL of sodium chloride.

6. The composition of claim 5 wherein the amount of dissolved oxygen is less than about 2 ppm.

7. The composition of claim 6 wherein the pH is about 4.0.

8. The composition of claim 5 wherein the concentration of cisplatin is about 1.0 mg/mL.

9. The composition of claim 8 wherein the tonicity of the composition has been adjusted with sodium chloride.

10. The composition of claim 4 wherein the vials are sealed with a stopper which has been treated with ethylenediamine tetraacetic acid to complex any heavy metals contained therein.

* * * * *